United States Patent
Yamaguchi et al.

(10) Patent No.: US 12,054,765 B2
(45) Date of Patent: Aug. 6, 2024

(54) PHYTOPATHOGENIC FUNGUS DETECTING APPARATUS, AND DETECTING METHOD AND METHOD FOR SELECTING CONCENTRATION OF AGRICULTURAL CHEMICAL USING SAME

(71) Applicant: Panasonic Intellectual Property Management Co., Ltd., Osaka (JP)

(72) Inventors: Kaori Yamaguchi, Fukui (JP); Shikiho Kawai, Hyogo (JP); Tarou Ishidou, Kyoto (JP); Yoshifumi Kariatsumari, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 958 days.

(21) Appl. No.: 17/079,405

(22) Filed: Oct. 23, 2020

(65) Prior Publication Data
US 2021/0040532 A1    Feb. 11, 2021

Related U.S. Application Data (63) Continuation of application No. PCT/JP2019/019998, filed on May 21, 2019.

(30) Foreign Application Priority Data

Jul. 9, 2018  (JP) .................. 2018-130065

(51) Int. Cl.
*C12Q 1/04*   (2006.01)
*C12M 1/32*  (2006.01)
(Continued)

(52) U.S. Cl.
CPC ............. *C12Q 1/045* (2013.01); *C12M 23/12* (2013.01); *C12M 23/42* (2013.01); *C12M 41/46* (2013.01)

(58) Field of Classification Search
None
See application file for complete search history.

(56) References Cited

U.S. PATENT DOCUMENTS

| 9,695,459 B2 | 7/2017 | Uriu |
| 2017/0096631 A1 | 4/2017 | Uematsu et al. |

(Continued)

FOREIGN PATENT DOCUMENTS

| CN | 2564584 Y | 8/2003 |
| CN | 203715637 U | 7/2014 |

(Continued)

OTHER PUBLICATIONS

International Search Report of PCT application No. PCT/JP2019/019998 dated Aug. 13, 2019.

(Continued)

*Primary Examiner* — Neil N Turk
(74) *Attorney, Agent, or Firm* — Rimon P.C.

(57) ABSTRACT

The detecting apparatus according to the present disclosure comprises devices each including an artificial cell wall, a test sample inlet provided above the artificial cell wall, and a culture medium layer provided under the artificial cell wall, and an observation part configured to laterally observe at least one of the culture medium layers of the devices, wherein the culture medium layers of the devises respectively contain different technical-grade active ingredients, each of the culture medium layers of the devices includes a plurality of layers that each contain an agricultural chemical in a standard amount or at a diluted concentration with respect to the standard amount and are stacked in a descending order of concentration of the agricultural chemical from bottom to top, and each of the culture medium layers of the devices further includes, as an uppermost layer, a layer containing no agricultural chemical.

10 Claims, 6 Drawing Sheets

(51) Int. Cl.
*C12M 1/34* (2006.01)
*C12M 3/00* (2006.01)

(56) References Cited

U.S. PATENT DOCUMENTS

| 2019/0048388 | A1 | 2/2019 | Yamaguchi et al. |
| 2021/0024874 | A1 | 1/2021 | Ishidou et al. |
| 2021/0040531 | A1 | 2/2021 | Ishidou et al. |
| 2021/0062237 | A1 | 3/2021 | Kariatsumari |

FOREIGN PATENT DOCUMENTS

| CN | 107820392 A | 3/2018 |
| CN | 111836879 A | 10/2020 |
| CN | 111836880 A | 10/2020 |
| CN | 112074595 A | 12/2020 |
| JP | 2005-287337 | 10/2005 |
| JP | 2015-177768 | 10/2015 |
| JP | 2017-073995 A | 4/2017 |
| JP | 6167309 B | 7/2017 |
| WO | WO2016109396 A1 | 7/2016 |
| WO | 2018/011835 | 1/2018 |

OTHER PUBLICATIONS

Paul F. Morris et al., "Chemotropic and Contact Responses of Phytophthora sojae Hyphae to Soybean Isoflavonoids and Artificial Substrates", Plant Physiol. (1998) 117: 1171-1178.

Hisashi Sakurai, "Methods of Determining the Drug-resistant Strains in Phytopathogenic Bacteria and Fungi and ts Epidemiology in the Field", Japanese Journal of Pesticide Science 2, 177-186 (1977).

English Translation of Chinese Search Report dated Oct. 24, 2023 for the related Chinese Patent Application No. 201980018548.X.

PHYTOPATHOGENIC FUNGUS DETECTING APPARATUS, AND DETECTING METHOD AND METHOD FOR SELECTING CONCENTRATION OF AGRICULTURAL CHEMICAL USING SAME

TECHNICAL FIELD

The present invention relates to a phytopathogenic fungus detecting apparatus having a function of selecting a concentration of an agricultural chemical, and to a pathogenic fungus detecting method and a method for selecting a concentration of an agricultural chemical using the phytopathogenic fungus detecting apparatus.

BACKGROUND ART

Phytopathogenic fungi have, as properties involving invasiveness into plants, features of forming an appressorium on a surface of a plant for attachment, and then searching for a pore, such as a stoma tissue, through which a hypha is extended into a plant body or secreting a plant cell wall degrading enzyme (a cellulase or a pectinase) from a hypha.

Making use of these features, for example, PTL 1 discloses a method for measuring an amount of a fungus using a microporous membrane support. NPL 1 discloses facts that a pseudohypha of *Phytophthora sojae* as one type of phytopathogenic oomycete grows downward as if attempting to go deep, rather than growing horizontally and that the pseudohypha penetrates a PET (polyethylene terephthalate) membrane having a pore of 3 μm.

Focusing on this property, the inventors of the present invention have already proposed a method for determining a phytopathogenic oomycete (PTL 2).

Further, a technique has also been reported that observes reproduction of a fungus at one time by scanning a plate having a plurality of wells, to perform a fixing inspection or a drug susceptibility inspection of a bacterium or a fungus (PTL 3).

CITATION LIST

Patent Literatures

PTL 1: Japanese Patent Application Publication No. 2005-287337
PTL 2: Japanese Patent No. 6,167,309
PTL 3: Japanese Patent Application Publication No. 2015-177768

Non-Patent Literature

NPL 1: Paul F. Morris. et. al. "Chemotropic and Contact Responses of *Phytophthora sojae* Hyphae to Soybean Isoflavonoids and Artificial Substrates", Plant Physiol. (1998) 117: 1171-1178

SUMMARY OF THE INVENTION

Technical Problems

The techniques (PTLs 1 and 2 and NPL 1) described in BACKGROUND ART enable a phytopathogenic fungus to be selectively detected but requires, in a plant cultivation site, a measure taken after the detection of the pathogenic fungus, that is, growth suppression or elimination of the pathogenic fungus by application of an agricultural chemical. In this regard, the conventional techniques that have been known so far presume a pathogenic fungus from symptoms of pathogenesis caused by the pathogenic fungus and apply a chemical, or separate or identify a pathogenic fungus and then apply a chemical, to cause a situation of being incapable of preventing spread of the pathogenic fungus. Alternatively, a measure is sometimes taken, for example, by excessively applying an agricultural chemical in advance assuming pathogenesis to make farm supervising operation hard. This excessive chemical application is recognized as leading to a result of promoting further emergence of a resistant fungus, and the present situation is that disease cannot be suppressed even with efforts, showing an example of falling into reduction of harvest or abandonment of crops.

The technique of PTL 3 has not studied about selection of an effective agricultural chemical and concentration of the agricultural chemical and employs a horizontal detecting method, which cannot be said as being efficient, for example, when the concentration of an agricultural chemical is selected.

The present invention has been made in view of such actual circumstances, and an object of the present invention is to provide a detecting apparatus capable of selectively determining whether or not a test sample contains a phytopathogenic fungus and proposing an effective agricultural chemical against the phytopathogenic fungus and an effective concentration of the agricultural chemical before pathogenesis of fungal disease, and to provide a detecting method and a method for selecting an effective concentration of an agricultural chemical.

Solutions to Problems

As a result of an earnest study, the inventors of the present invention and others have found that a detecting apparatus configured as below can solve the above problems and further conducted the study based on the finding to complete the present invention.

That is, a detecting apparatus related to one aspect of the present invention is a phytopathogenic fungus detecting apparatus comprising:
devices each including an artificial cell wall, a test sample inlet provided above the artificial cell wall, and a culture medium layer provided under the artificial cell wall; and
an observation part configured to laterally observe at least one of the culture medium layers of the devices,
wherein
the culture medium layers of the devises respectively contain different technical-grade active ingredients,
each of the culture medium layers of the devices includes a plurality of layers that each contain an agricultural chemical in a standard amount or at a diluted concentration with respect to the standard amount and are stacked in a descending order of concentration of the agricultural chemical from bottom to top, and
each of the culture medium layers of the devices further includes, as an uppermost layer, a layer containing no agricultural chemical.

Advantageous Effects of Invention

The present invention is capable of providing an apparatus and a method that are capable of selectively detecting a phytopathogenic fungus simply and safely. Further, the present invention enables an effective agricultural chemical and concentration of the agricultural chemical to be selected before pathogenesis of fungal disease. These effects not only save efforts such as wasteful spraying of an agricultural chemical or suppress excessive chemical application, but also prevent unnecessary spraying of a high-concentration agricultural chemical to potentially enable reduction in amounts of agricultural chemicals and thus be effective for, for example, suppressing residual amounts of agricultural chemicals.

DESCRIPTION OF EMBODIMENTS

Hereinafter, embodiments according to the present invention are specifically described. The present invention, however, is not limited to these embodiments.
(Detecting Apparatus)

Figure 1:
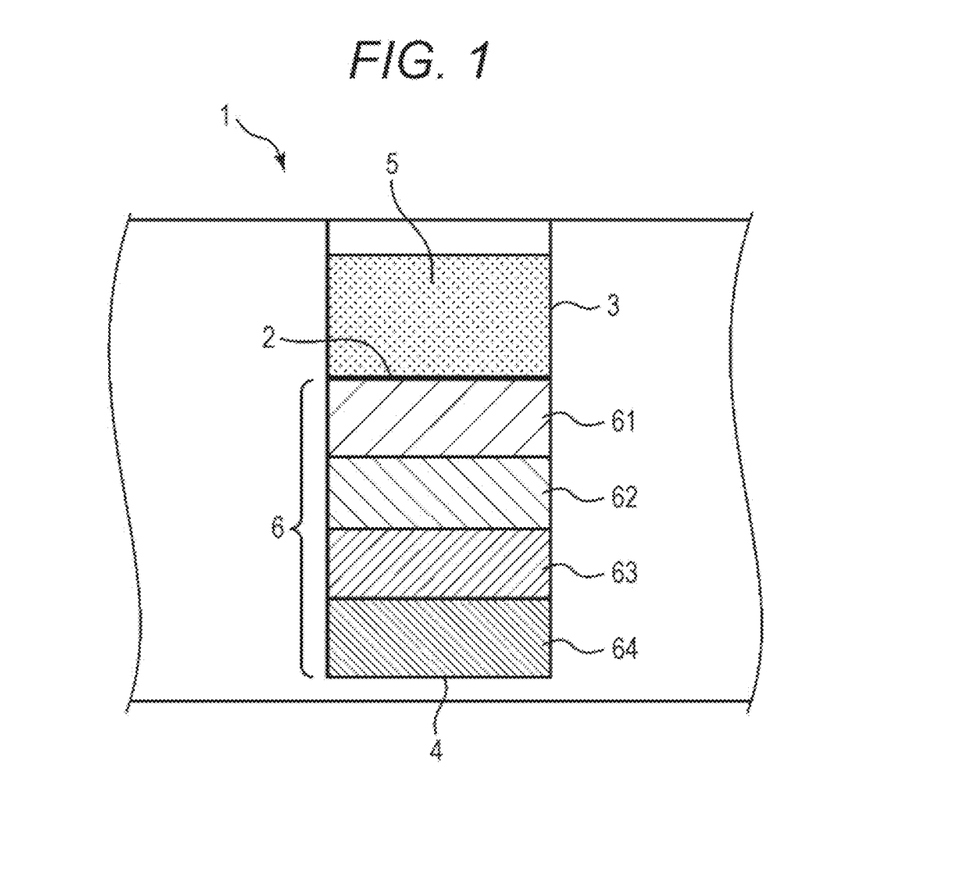
FIG. 1 shows a schematic sectional view illustrating a part of a detecting apparatus according to one embodiment of the present invention.
Figure 5:
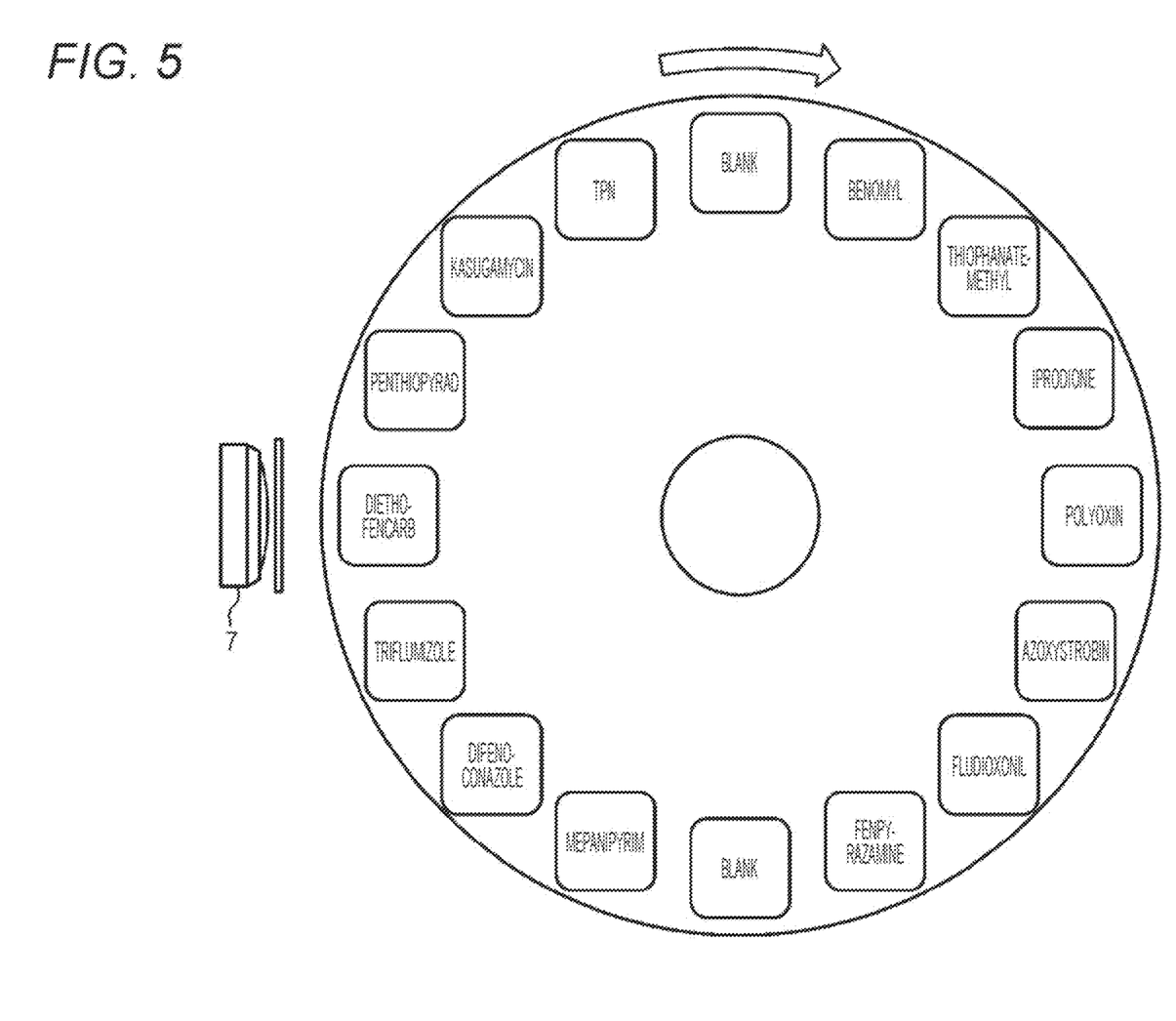
FIG. 5 shows a schematic view illustrating one example of detecting operation of the detecting apparatus according to the present embodiment illustrated in FIG. 3.
Figure 6:
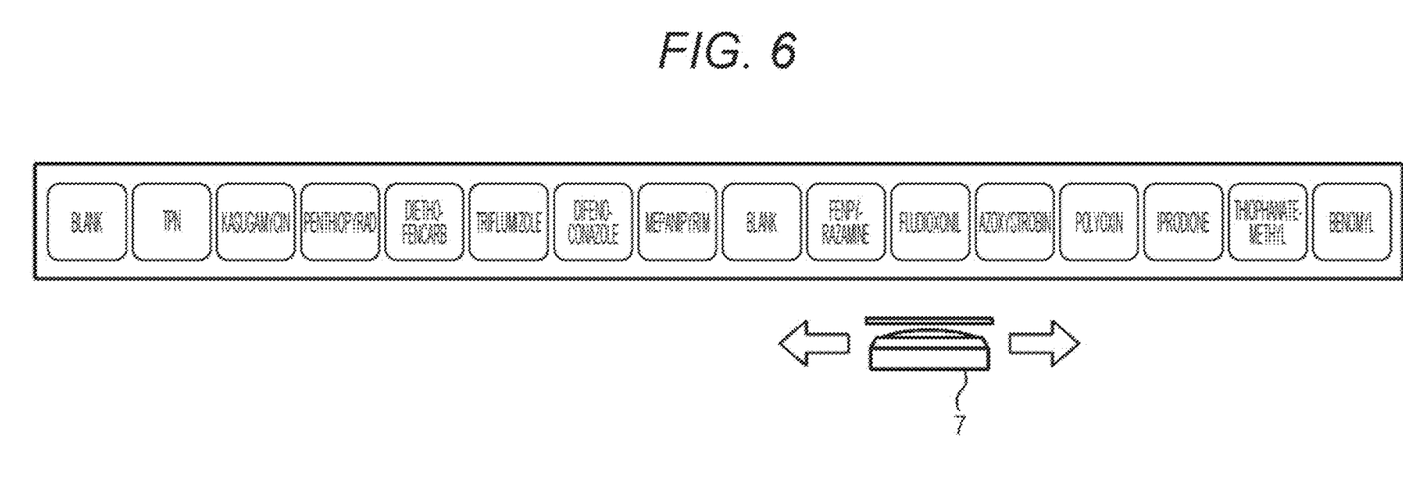
FIG. 6 shows a schematic view illustrating one example of detecting operation of the detecting apparatus according to the present embodiment illustrated in FIG. 4.

An apparatus according to the present embodiment that detects a phytopathogenic fungus includes devices 1 each including, as illustrated in FIG. 1, artificial cell wall 2, test sample inlet 3 provided above artificial cell wall 2, and culture layer 6 provided under artificial cell wall 2. Device 1 of the present embodiment can be rephrased as an incubator. Further, the apparatus of the present embodiment includes optical observation part 7 that is illustrated in FIGS. 5 and 6 below and that detects hyphal growth in each of the devices.

Culture medium layers 6 respectively contain different technical-grade active ingredients and each consist of a plurality of layers stacked in culture medium vessel 4. That is, the culture medium layer includes a plurality of layers that each contain an agricultural chemical in a standard amount or at a diluted concentration with respect to the standard amount and are stacked in a descending order of concentration of the agricultural chemical from bottom to top and further includes, as an uppermost layer, a layer containing no agricultural chemical. For example, in FIG. 1, there is chemical-free solid culture medium 61 on top of other layers, and under chemical-free solid culture medium 61 are stacked culture medium 62 with an agricultural chemical blended in an amount 1/50 a standard amount, culture medium 63 with the agricultural chemical blended in an amount 1/5 the standard amount, and culture medium 62 with the agricultural chemical blended in the standard amount in this order.

Test sample inlet 3 is a vessel into which test sample 5 is charged and a bottom surface of test sample inlet 3 is formed of artificial cell wall 2.

Figure 2:
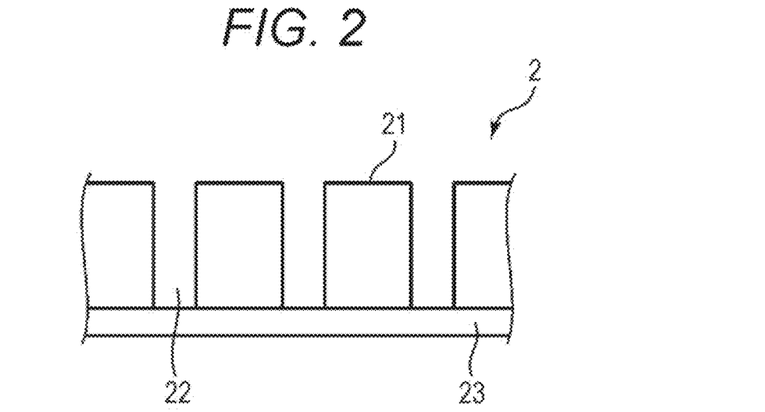
FIG. 2 shows a schematic sectional view illustrating one example of an artificial cell wall included in a device of the detecting apparatus according to the present embodiment.

Artificial cell wall 2 preferably includes, as illustrated in FIG. 2, at least substrate 21 having through hole 22, and cellulose membrane 23 provided on one surface of substrate 21. Use of such an artificial cell wall further facilitates selective detection of a targeted phytopathogenic fungus.

Through hole 22 penetrates from a front-end surface to a back-end surface of substrate 21, and the through hole preferably has a hole diameter of 2 µm to 7 µm (sectional area of 4.5 µm² to 38.5 µm²). The through hole having a hole diameter in the above range enables a target pathogenic fungus to be selectively detected more securely.

Further, in order to selectively detect a target pathogenic fungus more securely, a thickness of cellulose membrane 23 is also preferably adjusted. Specifically, cellulose membrane 23 preferably has a thickness of 0.5 µm to 2 µm.

It is considered that in artificial cell wall 2 of the present embodiment, adjusting the hole diameter of through hole 22 in substrate 21 and the membrane thickness of cellulose membrane 23 in the above range does not allow many of non-phytopathogenic fungi to penetrate cellulose membrane 23, but allows a pathogenic fungus targeted in the present embodiment to selectively appear on the back surface of cellulose membrane 23, so that a non-phytopathogenic fungus can be selectively detected.

A thickness of substrate 21 is not particularly limited, but is preferably about 5 µm to 150 µm as one example.

As illustrated in FIG. 1, test sample 5 is supplied into test sample inlet 3. Thus, if test sample 5 contains a phytopathogenic fungus, the phytopathogenic fungus comes to be present on the front-end surface of substrate 21.

In the present embodiment, test sample 5 is a solid, a liquid, or a gas. Test sample 5 is desirably a solid or a liquid. Examples of solid test sample 5 include soil and a crushed plant. Other examples include agricultural materials such as vermiculite, rock wool, and urethane. Examples of liquid test sample 5 include irrigation water, a solution used for hydroponic cultivation, a liquid having been used to wash a plant, a liquid extracted from a plant, a liquid having been used to wash an agricultural material, and a liquid having been used to wash clothes or shoes of a worker.

Alternatively, when an effective agricultural chemical is desired to be selected for a specific plant by checking which agricultural chemical is effective, a pathogenic fungus harmful to the plant is cultured in advance and a culture solution from the culture can be used as test sample 5.

Examples of the phytopathogenic fungus targeted by the detecting apparatus of the present embodiment include a tomato pathogenic fungus and other fungi belonging to a *Fusarium* genus, a *Pyricularia* genus, and a *Colletotrichum* genus. Examples of the tomato pathogenic fungus include a tomato gray mold fungus (*Botrytis cinerea*), a tomato sooty mold fungus (*Pseudocercospora fuligena*), and a tomato leaf mold fungus (*Passalora fulva*).

Other examples of the phytopathogenic fungus include *Fusarium oxysporum, Pyricularia grisea*, and *Colletotrichum gloeosporioides*. These phytopathogenic fungi cause root rot disease, blast disease, anthrax, gray mold disease, and the like. These phytopathogenic fungi kill plants. Examples of the non-phytopathogenic fungus include *Saccharomyces cerevisiae, Penicillium chysogeum*, and *Aspergillusoryzae*.

In the present embodiment, a targeted plant is preferably a tomato, which means that the targeted phytopathogenic fungus is preferably at least one selected from a tomato gray mold fungus (*Botrytis cinerea*), a tomato sooty mold fungus (*Pseudocercospora fuligena*), or a tomato leaf mold fungus (*Passalora fulva*).

In the present specification, the term "phytopathogenic" means being pathogenic to plants. The term "non-phytopathogenic" means being non-pathogenic to plants. A fungus that is pathogenic but is not pathogenic to plants is "non-phytopathogenic". In other words, a fungus that does not adversely affect plants is "non-phytopathogenic". The prefix "non-" included in the term "non-phytopathogenic" does not modify the "phyto", but modifies the "pathogenic".

In the detecting apparatus of the present embodiment, culture medium layer 6 provided under artificial cell wall 2 consists of a plurality of layers stacked in culture medium vessel 4 as described above. A culture medium used as culture medium layer 6 is not particularly limited as long as the culture medium is a culture solution capable of culturing a fungus, and a general culture medium or culture solution can be used. For example, a potato dextrose agar culture medium and a Sabouraud dextrose agar culture medium are usable, and the culture medium is desirable solid for stacking the plurality of layers. In order to accelerate the culture of a fungus, a culture solution may be added not only to culture medium layer 6 but also to test sample 5.

Culture medium vessel 4 is preferably a vessel composed of glass, a transparent resin, or the like for easy observation. A shape of the culture medium vessel is not particularly limited and may be of a cylindrical shape, a square or rectangular shape, or the like.

In the present embodiment, a technical-grade active ingredient is charged together with the culture medium into culture medium layer 6. If the apparatus includes a plurality of devices, different technical-grade active ingredients are respectively charged into the devices. Any technical-grade active ingredient is usable without particular limitation as long as the technical-grade active ingredient represents an agricultural chemical in question of being effective for a desired plant or not.

Examples of the usable technical-grade active ingredient include Kasugamycinhydrochloridemonohydrate, Mepanipyrim, Penthiopyrad, Triflumizole, Difenoconazole, Fenpyrazamine, Iprodione, Fludioxonil, Tetrachloroisophthalonitrile (TPN), Iminoctadinealbesilate, Captan, Tiophanete-methyl, Benomyl, Diethofencarb, Azoxystrobin, and Polioxin.

Culture medium layer 6 consists of a plurality of layers that contain a technical-grade active ingredient in different concentrations, respectively. When the test sample contains a pathogenic fungus, producing a concentration gradient of an agricultural chemical and disposing a chemical-free culture medium as an uppermost layer as described above allows the fungus having penetrated the artificial cell wall to extend a hypha further below the chemical-free culture medium. The concentration of the agricultural chemical in the layer where the hyphal growth is stopped can be determined to be an effective concentration of the agricultural chemical against the fungus. Meanwhile, if the fungus grows a hypha to the lowermost layer, the culture medium containing the agricultural chemical in the standard amount, the technical-grade active ingredient is determined to be ineffective against the fungus.

FIG. 1 illustrates culture medium layer 6 including four layers, but a number of layers included in the culture medium layer is not particularly limited and can be appropriately set as necessary. In addition, with regard to the concentration of an agricultural chemical contained in each of the layers, the concentration of the agricultural chemical in intermediate layer(s) can be appropriately set as long as the lower most layer is set for the standard amount, a plurality of layers that each contain an agricultural chemical at a diluted concentration with respect to the standard amount are stacked in a descending order of concentration of the agricultural chemical from bottom to top, and the layer containing no agricultural chemical is included as the uppermost layer.

The detecting apparatus of the present embodiment enables presence or absence of a phytopathogenic fungus in a sample to be detected by observing, after a lapse of a certain culture period, whether or not the phytopathogenic fungus has appeared in the culture medium layer in contact with the back surface of cellulose membrane 23 of artificial cell wall 2. The detecting apparatus also enables effectiveness of a technical-grade active ingredient contained in the device to be confirmed according to the appearance or non-appearance of a fungus. Further, the detecting apparatus enables an effective concentration of the agricultural chemical to be determined by observing to which culture medium layer a hypha of the fungus has grown.

For the observation, the detecting apparatus of the present embodiment includes optical observation part 7 illustrated in FIGS. 5 and 6 beside (before) devices 1. As optical observation part 7, an optical microscope is usable.

The culture period of a fungus is not particularly limited and is changed according to the number of stacked agricultural-chemical culture media or a thickness of each of the layers. The culture period, however, is normally preferably not less than 72 hours. A culture temperature is preferably set at about 20° C. to 28° C.

Figure 3:
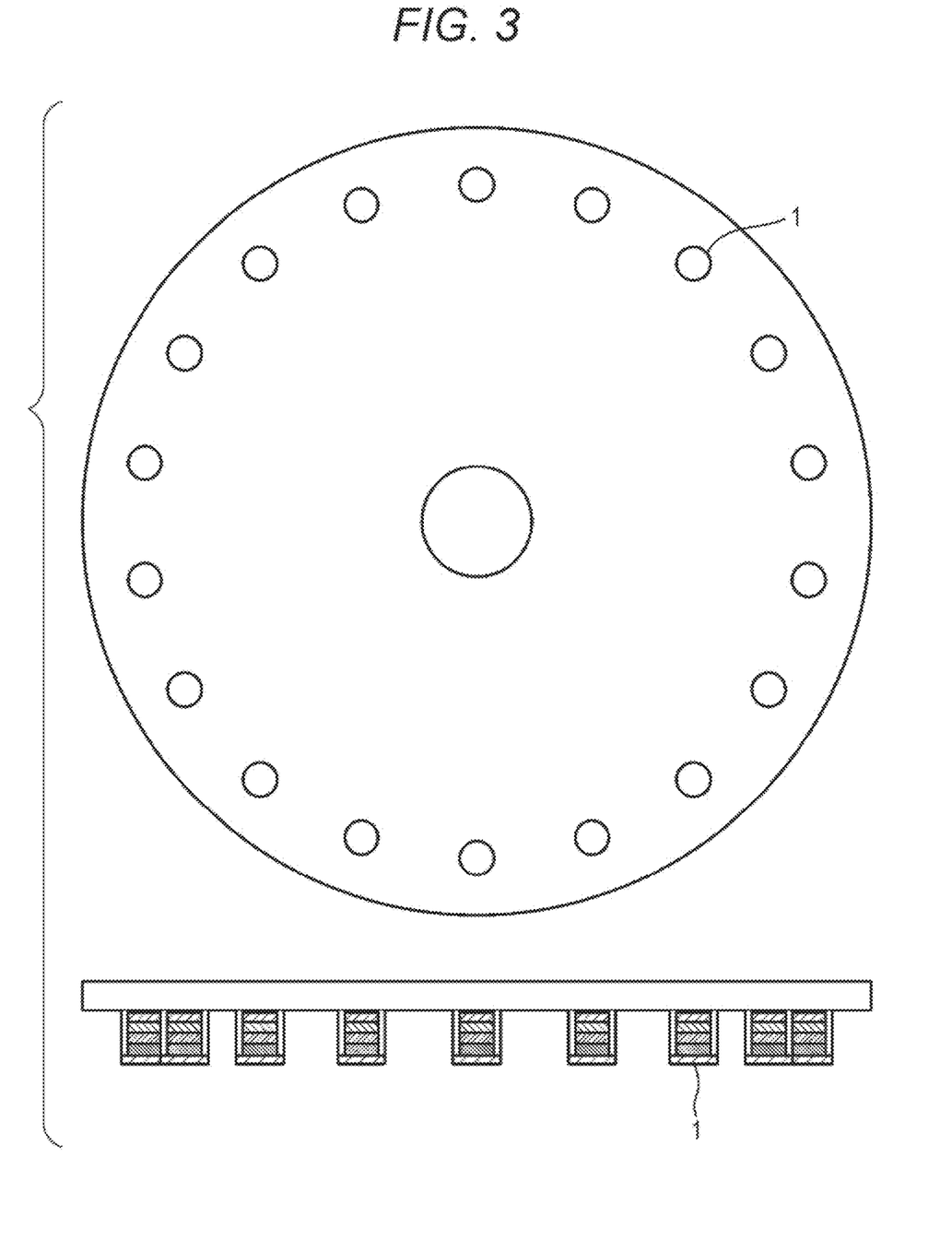
FIG. 3 shows a top view (upper) and a sectional view (lower) illustrating one example of the detecting apparatus according to the present embodiment.
Figure 4:
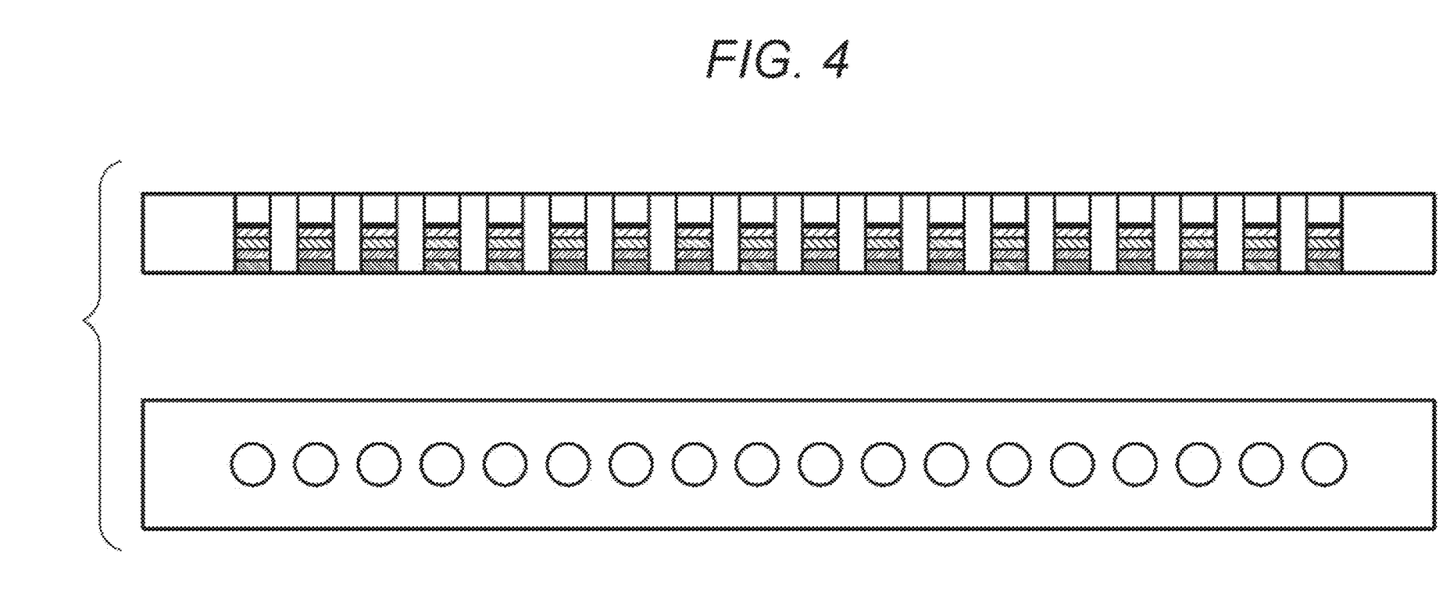
FIG. 4 shows a sectional view (upper) and a top view (lower) illustrating one example of a detecting apparatus according to another embodiment of the present invention.

The detecting apparatus of the present embodiment includes a plurality of devices 1 each composed of at least test sample inlet 3, artificial cell wall 2, and culture medium layer 6 that are illustrated in FIG. 1. With regard to disposition or arrangement of the plurality of devices 1, the devices may be disposed, for example, circumferentially as illustrated in FIG. 3 or can also be disposed in series as illustrated in FIG. 4. The disposition of devices 1 is not particularly limited as long as the disposition enables the optical observation part to transversely observe the culture medium layer.

FIG. 3 shows a top view (upper) and a sectional view (lower) of circumferential disposition of devices 1 of the present embodiment. FIG. 4 shows a sectional view (upper) and a top view (lower) of serial disposition of devices 1 of the present embodiment.

The detecting apparatus of the present embodiment preferably includes the plurality of devices described above, and the culture medium layer of at least one device among the plurality of devices preferably contains no technical-grade active ingredient. For example, the device illustrated as "blank" in FIGS. 5 and 6 below contains no technical-grade active ingredient. One blank device or a plurality of blank devices can be provided. A position of the blank device is preferably to be recognized and distinguished.

When the detecting apparatus of the present embodiment includes the plurality of devices disposed circumferentially, it is preferable that as illustrated in FIG. 5, the circumferentially disposed devices are horizontally rotated, and optical observation part 7 is fixed to a specific place and transversely observes each of devices 1 as regards whether or not a fungus has appeared in culture medium layer 6 when the device reaches optical observation part 7 by the rotation.

When the plurality of devices are disposed in series, not the devices but optical observation part 7 may be laterally moved to observe each of the devices as illustrated in FIG. 6.

Thus, one optical observation part 7 is enough for installation in both the cases, and remaining selection is whether the devices are rotated or optical observation part 7 is moved, to enable presence or absence of a fungus in culture medium layer 6 to be detected.

The detection (optical observation) is preferably started from a blank device (containing no technical-grade active ingredient). The blank device is first observed, and if hyphal growth is not confirmed there, it is possible to determine the absence of a pathogenic fungus in the test sample and stop the following detection. Only if hyphal growth is confirmed in the blank device, the following devices can be detected sequentially as regards whether or not each technical-grade active ingredient is effective. Therefore, this detecting way is efficient and enables cost saving.

A disposition order of technical-grade active ingredients is not particularly limited, but it is preferable to prepare and dispose the technical-grade active ingredients from a technical-grade active ingredient recognized as having a low resistance risk. Specifically, for example, when a tomato pathogenic fungus is detected, TPN, Captan, Iminoctadinealbesilate, Fenpyrazamine, and Fludioxonil are preferably disposed in this order. Thereafter, technical-grade active ingredients having a middle to high resistance risk (=likely to allow a resistant fungus to emerge) are desirably disposed. Specifically, Kasugamycin, Mepanipyrim, Penthiopyrad, Azoxystrobin, Polyoxin, Triflumizole, Difenoconazole, Iprodione, Tiophanete-methyl, Benomyl, and Diethofencarb are preferably disposed in this order.

A number of technical-grade active ingredients is different according to the pathogenic fungus to be targeted. For example, when only a tomato sooty mold fungus (*Pseudocercospora fuligena*) is a detection target, the number of technical-grade active ingredients can be reduced to as less as five types of technical-grade active ingredients.

The detecting apparatus described above of the present embodiment is capable of proposing an effective agricultural chemical and an effective concentration of the agricultural chemical from growth situations of a fungus in the devices. Further, effective patterns of agricultural chemicals are considered to enable identification of the type of a pathogenic fungus. Furthermore, accumulation and organization of data of detection results are considered to enable suggestion of emergence of a resistant strain in fungi.

(Pathogenic Fungus Detecting Method)

The present invention further encompasses a phytopathogenic fungus detecting method including selectively detecting a phytopathogenic fungus using the detecting apparatus described above.

The phytopathogenic fungus detecting method of the present embodiment is not particularly limited in terms of steps other than using the detecting apparatus described above, and includes the steps of, for example: charging a test sample into test sample inlet 3 of the detecting apparatus; leaving the test sample to stand still in the detecting apparatus (culturing); observing a lower portion of artificial cell wall 2 (cellulose membrane 23) in the detecting apparatus after the leaving; and determining that the test sample contains a phytopathogenic fungus when a hypha of the fungus is observed on the lower portion of cellulose membrane 23 or culture medium layer 6.

(Method for Selecting Agricultural Chemical and Effective Concentration of Agricultural Chemical)

The present invention further encompasses a method for selecting a concentration of an agricultural chemical, the method selecting an effective technical-grade active ingredient and concentration of the agricultural chemical using the detecting apparatus described above.

The method of the present embodiment for selecting a concentration of an agricultural chemical is not particularly limited in terms of steps other than using the detecting apparatus described above, and preferably includes at least the steps of, for example:

respectively charging different technical-grade active ingredients into layers other an uppermost layer of culture medium layers 6 in a plurality of devices except a blank device in a standard amount or at a diluted concentration with respect to the standard amount;

charging test sample 5 into test sample inlet 3 of the blank device, leaving test sample 5 to stand still in the detecting apparatus (culturing), and observing culture medium layer 6 in the detecting apparatus after the leaving;

recognizing test sample 5 as containing a phytopathogenic fungus and moving the device when the fungus is observed in culture medium layer 6, and observing culture medium layer 6 in a device containing a next technical-grade active ingredient as regards to which layer the fungus has grown a hypha; and determining that a concentration of an agricultural chemical in a layer of culture medium layer 6 where the hyphal growth is stopped is an effective concentration of the agricultural chemical against the fungus.

The present specification discloses various forms of techniques as described above, from among which main techniques are summarized as follows.

A phytopathogenic fungus detecting apparatus according to one aspect of the present invention is a phytopathogenic fungus detecting apparatus comprising devices each including an artificial cell wall, a test sample inlet provided above the artificial cell wall, and a culture medium layer provided under the artificial cell wall, and an observation part configured to laterally observe at least one of the culture medium layers of the devices, wherein the culture medium layers of the devises respectively contain different technical-grade active ingredients, each of the culture medium layers of the devices includes a plurality of layers that each contain an agricultural chemical in a standard amount or at a diluted concentration with respect to the standard amount and are stacked in a descending order of concentration of the agricultural chemical from bottom to top, and each of the culture medium layers of the devices further includes, as an uppermost layer, a layer containing no agricultural chemical.

These configurations enable provision of an apparatus and a method that are capable of selectively detecting a phytopathogenic fungus simply and safely. Further, these configurations enable selection of an effective agricultural chemical and concentration of the agricultural chemical before pathogenesis of fungal disease. These effects not only save efforts such as wasteful spraying of an agricultural chemical or suppress excessive chemical application, but also prevent unnecessary spraying of a high-concentration agricultural chemical to potentially enable reduction in amounts of agricultural chemicals and thus be effective for, for example, suppressing residual amounts of agricultural chemicals.

In the detecting apparatus, it is preferable that the artificial cell wall includes at least a substrate that has a through hole with a hole diameter of 2 μm to 7 μm and has a thickness of 5 μm to 150 μm, and a cellulose membrane that is provided on one surface of the substrate and has a thickness of 0.5 μm to 2 μm. These configurations are considered to enable the effects described above to be more securely obtained.

Further, in the detecting apparatus, the plurality of devices are preferably disposed circumferentially or in series. This arrangement further facilitates transverse observation of the culture medium layer of each of the devices.

Further, in the detecting apparatus, the culture medium layer of at least one device among the plurality of devices preferably contains no technical-grade active ingredient. Such a configuration gives an advantage of enabling quick determination of absence of a pathogenic fungus when a test sample contains no pathogenic fungus, and skipping a following wasteful inspection.

Furthermore, in the detecting apparatus, it is preferable that the devices are moved and the observation part is fixed and transversely observes each of the devices. These configurations are considered to enable the effects described above to be more efficiently obtained.

Furthermore, in the detecting apparatus, it is preferable that a targeted plant is a tomato and a detection target is at least one selected from a tomato gray mold fungus (*Botrytis cinerea*), a tomato sooty mold fungus (*Pseudocercospora fuligena*), or a tomato leaf mold fungus (*Passalora fulva*). This setting is considered to enable the effects described above to be more exhibited.

The technical-grade active ingredient contained in the culture medium layer is preferably at least one selected from the group consisting of Kasugamycinhydrochloridemonohydrate, Mepanipyrim, Penthiopyrad, Triflumizole, Difenoconazole, Fenpyrazamine, Iprodione, Fludioxonil, Tetrachloroisophthalonitrile (TPN), Iminoctadinealbesilate, Captan, Tiophanete-methyl, Benomyl, Diethofencarb, Azoxystrobin, and Polioxin. This setting is considered to enable the effects described above to be more exhibited.

A phytopathogenic fungus detecting method according to another aspect of the present invention is characterized by including selectively detecting a phytopathogenic fungus using the detecting apparatus described above.

A method according to another aspect of the present invention for selecting an agricultural chemical is characterized by including selecting an effective concentration of an agricultural chemical using the detecting apparatus described above.

Hereinafter, the present invention is described further specifically by way of an example. A scope of the present invention, however, is not limited to this example.

Example (Culture of *Botrytis cinerea*)

*Botrytis cinerea* that is one type of phytopathogenic fungus and a pathogenic fungus of tomato gray mold disease was inoculated into a potato dextrose agar culture medium (Difco (registered trademark) Potato Dextrose Agar). Next, the culture medium was left to stand still at a temperature of 25 degrees Celsius for one week. *Botrytis cinerea* was given by associate professor Shimizu belonging to Faculty of Applied Biological Sciences, Gifu University. Next, the *Botrytis cinerea*-cultured potato dextrose agar culture medium in which hyphae sufficiently grew was left under irradiation with black light for not less than four days and left in a room-temperature environment for not less than two weeks to promote spore formation. Several ml of sterile pure water was dropped to the treated *Botrytis cinerea*-cultured potato dextrose agar culture medium, and surfaces of the hyphae were rubbed with a platinum loop, an ink brush, or the like to give a crushed hypha and spore mixed suspension. Hereinafter, this aqueous solution is referred to as an "aqueous phytopathogenic fungus solution".

(Preparation of Agricultural-Chemical Three-Concentration-Level Layers-Stacked Culture Media)

Agricultural-chemical main-ingredient reagent Captan (manufactured by Tokyo Chemical Industry Co., Ltd. (TCI)) was added to potato dextrose agar culture media, with a charging amount (concentration) changed, to produce three layers of original culture media. Captan was prepared into a dimethyl sulfoxide (DMSO) (manufactured by SIGMA-ALDRICH) solution of Captan at a concentration 100 times a standard use concentration. The solution was charged into and mixed with the potato dextrose agar culture media respectively in amounts of 0 ml, 2 ml, and 10 ml per 1 L of the potato dextrose agar culture media to make three-concentration-level culture media respectively at a Captan concentration of 0 (no blending) and in an amount ⅕ a standard use amount of Captan and the standard use amount. In the present example, the potato dextrose agar culture media containing Captan at three concentration levels were stacked from bottom in an order of the Captan standard amount culture medium, the culture medium in an amount ⅕ the Captan standard amount, and the medium with no Captan blended, and the stacked body was cut out with a glass cylindrical, square, or rectangular shape forming member into a device of the example.

(Preparation of Layers-Stacked Culture Media Containing No Agricultural Chemical)

Further, for a purpose of comparison, three layers of potato dextrose agar culture media containing no Captan were shape-formed similarly to the above for use as a device (blank) including a culture medium layer that consists of only culture media containing no agricultural chemical.

(Addition of Aqueous Phytopathogenic Fungus Solution to Devices and Culture)

Two hundred microliters of the aqueous phytopathogenic fungus solution containing 200 pieces of hyphae and spores of *Botrytis cinerea* were added onto an uppermost portion of each of the device (Example 1) housing the agricultural-chemical three-concentration-level layers-stacked culture media in the device and the device (blank) housing the layers-stacked culture media containing no agricultural chemical, that is, onto the potato dextrose agar culture medium containing no Captan regarding the agricultural-chemical three-concentration-level layers-stacked culture media.

Each of the devices to which the aqueous phytopathogenic fungus solution was added was left to stand still at a temperature of 25 degrees Celsius for seven days to culture the phytopathogenic fungus.

(Results and Consideration)

Figure 7:
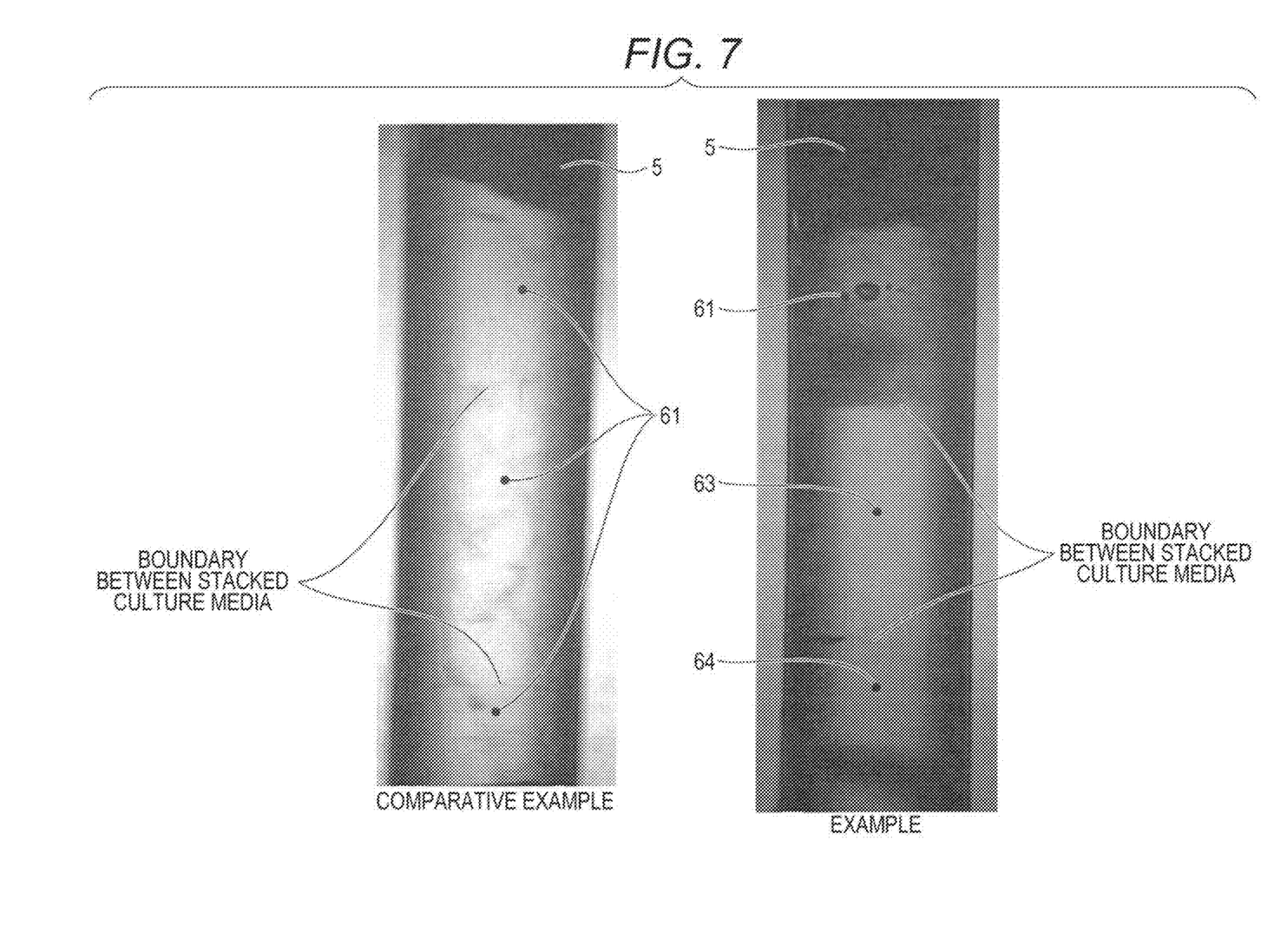
FIG. 7 shows microphotographs illustrating a result of an example.

After the culture, the device of the example and the blank device were each observed at the layers-stacked agar culture media from a side surface of the transparent member with a microscope. FIG. 7 shows microphotographs of the observation. The left microphotograph is a result of the blank device, and the right photograph is a result of the device in the example.

As illustrated in FIG. 7, visual inspection via the optical microscope found a state where hyphae from *Botrytis cinerea* hyphal mass 5 on the top invaded into the layers-stacked agar culture media of each of the devices and grew.

In the photograph of the blank device, the hyphae of *Botrytis cinerea* are observed to have reached up to the third layer in the layers-stacked potato dextrose agar culture media. On the other hand, the device of the example is observed to have allowed active invasion of the hyphae of *Botrytis cinerea* and reproduction of the hyphae in the culture medium of a surface layer, i.e., layer 61 with no Captan blended, but no hypha of *Botrytis cinerea* was confirmed in the culture medium of the second layer, i.e., layer 63 with Captan blended in the amount ⅕ the standard use amount, and layer 63 remained transparent. No hypha was confirmed also in subsequently lower layer 64 with Captan blended in the standard amount. This result indicates that agricultural-chemical ingredient Captan exerted an effect against *Botrytis cinerea* with the amount ⅕ the standard use amount.

The test described above indicated that the present invention is capable of selectively determining whether or not a test sample contains a phytopathogenic fungus and proposing an effective concentration of an agricultural chemical against the phytopathogenic fungus. This result can lead to a possibility of reducing an amount of the agricultural chemical.

INDUSTRIAL APPLICABILITY

A phytopathogenic fungus detecting apparatus according to the present disclosure that has a function of selecting an agricultural chemical is capable of selectively determining whether or not a test sample contains a phytopathogenic fungus and proposing an effective concentration of an agricultural chemical against the phytopathogenic fungus before pathogenesis of fungal disease. Therefore, the detecting apparatus of the present disclosure can be suitably utilized in various technical fields such as agriculture.

REFERENCE SIGNS LIST 1 device
2 artificial cell wall
3 test sample inlet
4 culture medium vessel
5 test sample
6 culture medium layer
7 optical observation part
21 substrate
22 through hole
23 cellulose membrane
61 chemical-free culture medium layer
62 culture medium layer with agricultural chemical blended in amount ¹⁄₅₀ standard amount
63 culture medium layer with agricultural chemical blended in amount ⅕ standard amount
64 culture medium layer with agricultural chemical blended in standard amount

The invention claimed is:

1. A phytopathogenic fungus detecting apparatus comprising:
a plurality of devices, each including a vessel having an upper opening as a test sample inlet and a bottom, an artificial cell wall disposed in the vessel, and a culture medium layer provided between the artificial cell wall and the bottom of the vessel; and
an observation part disposed such that the positions of the observation part and the plurality of devices are relatively movable, and being configured to laterally observe at least a part of the culture medium layer of one or more of the plurality of devices, wherein;
the culture medium layer of each of the plurality of devices includes a plurality of sub-layers each of which contains a technical-grade active ingredient,
a material of the technical-grade active ingredient in the culture medium layer of one of the plurality of devices is different from a material of the technical-grade active ingredient in the culture medium layer of another of the plurality of devices,
a concentration of the technical-grade active ingredient at a bottommost one of the plurality of sub-layers closest to the bottom of the vessel is a standard amount, and remaining ones of the plurality of sub-layers have a diluted concentration with respect to the standard amount and are stacked in a descending order of concentration of the technical-grade active ingredient from a position above the bottommost one of the plurality of sub-layer to a position below to the artificial cell wall, and
the culture medium layer of each of the plurality of devices further includes, as an uppermost layer, a layer containing no technical-grade active ingredient.

2. The phytopathogenic fungus detecting apparatus according to claim 1, wherein
the artificial cell wall includes a substrate that has a through hole with a hole diameter of 2 μm to 7 μm and has a thickness of 5 μm to 150 μm, and
a cellulose membrane that is provided on one surface of the substrate and has a thickness of 0.5 μm to 2 μm.

3. The phytopathogenic fungus detecting apparatus according to claim 1, wherein the plurality of devices are circumferentially disposed.

4. The phytopathogenic fungus detecting apparatus according to claim 1, wherein the plurality of devices are linearly disposed.

5. The phytopathogenic fungus detecting apparatus according to claim 3, further comprising
a blank device in which the culture medium layer contains no technical-grade active ingredient.

6. The phytopathogenic fungus detecting apparatus according to claim 1, wherein
the observation part is fixed and configured to transversely observe each of the plurality of devices, and
either one of the following requirements is satisfied:
(I) the phytopathogenic fungus detecting apparatus includes a disk to which the plurality of devices are provided, and the phytopathogenic fungus detecting apparatus is rotatable, or
(II) the phytopathogenic fungus detecting apparatus includes a line-shape support to which the plurality of devices are provided, and the phytopathogenic fungus detecting apparatus is slidable.

7. The phytopathogenic fungus detecting apparatus according to claim 6, wherein a targeted plant is a tomato.

8. The phytopathogenic fungus detecting apparatus according to claim 7, wherein a detection target is at least one selected from the group consisting of tomato gray mold fungus *Botrytis cinerea*, tomato sooty mold fungus *Pseudocercospora fuligena*, and tomato leaf mold fungus *Passalora fulva*.

9. The phytopathogenic fungus detecting apparatus according to claim 1, wherein the technical-grade active ingredient is at least one selected from the group consisting of Kasugamycinhydrochloridemonohydrate, Mepanipyrim, Penthiopyrad, Triflumizole, Difenoconazole, Fenpyrazamine, Iprodione, Fludioxonil, Tetrachloroisophthalonitrile TPN, Iminoctadinealbesilate, Captan, Tiophanete-methyl, Benomyl, Diethofencarb, Azoxystrobin, and Polioxin.

10. A cultivating device comprising:
a vessel having an upper opening as a test sample inlet and a bottom;
an artificial cell wall disposed in the vessel; and
a culture medium layer provided between the artificial cell wall and the bottom of the vessel, wherein:
the culture medium layer of includes a plurality of sub-layers each of which contains a technical-grade active ingredient and a top layer disposed over the plurality of sub-layers,
a concentration of the technical-grade active ingredient at a bottommost one of the plurality of sub-layers closest to the bottom of the vessel is a standard amount, and remaining ones of the plurality of sub-layers have a diluted concentration with respect to the standard amount and are stacked in a descending order of concentration of the technical-grade active ingredient from a position above the bottommost one of the plurality of sub-layer to a position below to the artificial cell wall, and
the top layer contains no technical-grade active ingredient.

* * * * *